(12) United States Patent
Lin et al.

(10) Patent No.: US 6,797,825 B2
(45) Date of Patent: Sep. 28, 2004

(54) PROTEIN KINASE INHIBITORS

(75) Inventors: Nan-Horng Lin, Vernon Hills, IL (US); Hing L. Sham, Vernon Hills, IL (US); Ping Xia, St. Louis, MO (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/317,336

(22) Filed: Dec. 12, 2002

(65) Prior Publication Data
US 2003/0162785 A1 Aug. 28, 2003

Related U.S. Application Data

(60) Provisional application No. 60/341,410, filed on Dec. 13, 2001.

(51) Int. Cl.$^7$ ............................................. C07D 471/02
(52) U.S. Cl. ..................... 546/113; 548/455; 546/277.4
(58) Field of Search ............................. 546/113, 277.4; 548/455

(56) References Cited

U.S. PATENT DOCUMENTS

| | | | |
|---|---|---|---|
| 5,629,325 A | 5/1997 | Lin et al. |
| 5,792,783 A | 8/1998 | Tang et al. |
| 5,883,116 A | 3/1999 | Tang et al. |
| 5,935,977 A | 8/1999 | Yamazaki et al. |
| 6,147,106 A | 11/2000 | Tang et al. |
| 6,225,335 B1 | 5/2001 | Tang et al. |
| 6,316,429 B1 | 11/2001 | Tang et al. |
| 6,316,635 B1 | 11/2001 | Tang et al. |
| 2001/0044451 A1 | 11/2001 | Fraley et al. |

FOREIGN PATENT DOCUMENTS

| | | |
|---|---|---|
| DE | 19949209 | 4/2001 |
| EP | 0741707 | 4/1998 |
| WO | 95/17181 | 6/1995 |
| WO | 96/00226 * | 1/1996 |
| WO | 96/10012 | 4/1996 |
| WO | 97/30044 | 8/1997 |
| WO | 97/46551 | 12/1997 |
| WO | 98/02434 | 1/1998 |
| WO | 98/38984 | 9/1998 |
| WO | 99/10325 | 3/1999 |
| WO | 99/15500 | 4/1999 |
| WO | 99/61422 | 12/1999 |
| WO | 99/65875 | 12/1999 |
| WO | 00/12084 | 3/2000 |
| WO | 00/18734 | 4/2000 |
| WO | 00/38519 | 7/2000 |
| WO | 00/49015 | 8/2000 |
| WO | 00/56709 | 9/2000 |
| WO | 01/16130 | 3/2001 |
| WO | 01/27081 | 4/2001 |
| WO | 01/30151 | 5/2001 |
| WO | 01/49287 | 7/2001 |
| WO | 01/55116 | 8/2001 |
| WO | 01/60814 | 8/2001 |
| WO | 01/60816 | 8/2001 |
| WO | 01/62251 | 8/2001 |
| WO | 01/62252 | 8/2001 |
| WO | 01/66708 | 9/2001 |
| WO | 01/83450 | 11/2001 |
| WO | 01/90103 | 11/2001 |
| WO | 01/90104 | 11/2001 |
| WO | 01/94312 | 12/2001 |

* cited by examiner

Primary Examiner—Joseph K. McKane
Assistant Examiner—Andrea D Small
(74) Attorney, Agent, or Firm—Gregory W. Steele

(57) ABSTRACT

Compounds having the formula

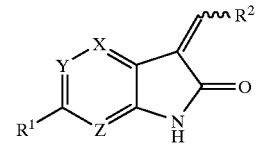

or therapeutically acceptable salts thereof, are protein kinase inhibitors. Preparation of the compounds, compositions containing the compounds, and treatment of diseases using the compounds are disclosed.

5 Claims, No Drawings

PROTEIN KINASE INHIBITORS

This application claims priority to the U.S. Provisional Application Serial No. 60/341,410, filed Dec. 13, 2001.

TECHNICAL FIELD

The present invention relates to substituted indalones which are useful for inhibiting protein kinases, methods of making the compounds, compositions containing the compounds, and methods of treatment using the compounds.

BACKGROUND OF THE INVENTION

Protein kinases have been clearly shown to be important in the progression of many disease states that are induced by the inappropriate proliferation of cells. These kinases are often found to be up-regulated in many hyperproliferative states such as cancer. These kinases may be important in cell signaling, where their inappropriate activation induces cells to proliferate (e.g. EGFR, ERBB2, VEGFR, FGFR, PDGFR, c-Met, IGF-1R, RET, TIE2). Alternatively, they may be involved in signal transduction within cells (e.g. c-Src, PKC, Akt, PKA, c-Ab1, PDK-1). Often these signal transduction genes are recognized proto-oncogenes. Many of these kinases control cell cycle progression near the G1-S transition (e.g. Cdk2, Cdk4), at the G2-M transition (e.g. Wee1, Myt1, Chk1, Cdc2) or at the spindle checkpoint (P1k, Aurora1 or 2, Bub1 or 3). Furthermore, kinases are intimately linked to the DNA damage response (e.g. ATM, ATR, Chk1, Chk2). Disregulation of these cellular functions; cell signaling, signal transduction, cell cycle control, and DNA repair, are all hallmarks of hyperproliferative diseases, particularly cancer. It is therefore likely that pharmacological modulation of one or more kinases would be useful in slowing or stopping disease progression in these diseases.

SUMMARY OF THE INVENTION

In its principle embodiment, the present invention provides a compound of formula (I)

$$(I)$$

or a therapeutically acceptable salt thereof, wherein
  X is selected from the group consisting of —N— and —CR$^x$—;
  Y is selected from the group consisting of —N— and —CR$^y$—;
  Z is selected from the group consisting of —N— and —CR$^z$—;
with the proviso that at least one of Y and Z is other than —N—;
  one of R$^x$, R$^y$, R$^z$, and R$^1$ is selected from the group consisting of aryl and heterocycle and the others are hydrogen; and
  R$^2$ is selected from the group consisting of heterocycle and aryl; with the proviso that when R$^2$ is heterocycle the heterocycle is other than imidazolyl.

DETAILED DESCRIPTION OF THE INVENTION

As used in the present specification the following terms have the meanings indicated:

The term "alkoxy," as used herein, refers to an alkyl group attached to the parent molecular moiety through an oxygen atom.

The term "alkoxyalkyl," as used herein, refers to an alkoxy group attached to the parent molecular moiety through an alkyl group.

The term "alkoxycarbonyl," as used herein, refers to an alkoxy group attached to the parent molecular moiety through a carbonyl group.

The term "alkoxycarbonylalkyl," as used herein, refers to an alkoxycarbonyl group attached to the parent molecular moiety through an alkyl group.

The term "alkyl," as used herein, refers to a monovalent group of one to twelve carbon atoms derived from a straight or branched chain saturated hydrocarbon.

The term "alkylcarbonyl," as used herein, refers to an alkyl group attached to the parent molecular moiety through a carbonyl group.

The term "alkylcarbonyloxy," as used herein, refers to an alkylcarbonyl group attached to the parent molecular moiety through an oxygen atom.

The term "amino," as used herein, refers to —NR$^a$R$^b$, wherein R$^a$ and R$^b$ are independently selected from the group consisting of hydrogen, alkyl, alkylcarbonyl, cycloalkyl, (cycloalkyl)alkyl, and unsubstituted phenyl.

The term "aminoalkyl," as used herein, refers to an amino group attached to the parent molecular moiety through an alkyl group.

The term "aryl," as used herein, refers to a phenyl group, or a bicyclic or tricyclic fused ring system wherein one or more of the fused rings is a phenyl group. Bicyclic fused ring systems are exemplified by a phenyl group fused to a cycloalkenyl group, as defined herein, a cycloalkyl group, as defined herein, or another phenyl group. Tricyclic fused ring systems are exemplified by a bicyclic fused ring system fused to a cycloalkenyl group, as defined herein, cycloalkyl group, as defined herein, or another phenyl group. Representative examples of aryl include, but are not limited to, anthracenyl, azulenyl, fluorenyl, indanyl, indenyl, naphthyl, phenyl, and tetrahydronaphthyl. The aryl groups of the present invention can be optionally substituted with one, two, three, four, or five substituents independently selected from the group consisting of alkoxy, alkoxyalkyl, alkoxycarbonylalkyl, alkylcarbonyloxy, alkyl, amino, aminoalkyl, cyano, halo, haloalkoxy, haloalkyl, hydroxy, hydroxyalkyl, nitro, and oxo.

The term "carbonyl," as used herein, refers to —C(O)—.

The term "cyano," as used herein, refers to —CN.

The term "cycloalkenyl," as used herein, refers to a non-aromatic cyclic or bicyclic ring system having three to ten carbon atoms and one to three rings, wherein each five-membered ring has one double bond, each six-membered ring has one or two double bonds, each seven- and eight-membered ring has one to three double bonds, and each nine-to ten-membered ring has one to four double bonds. Representative cycloalkenyl groups include, but are not limited to, cyclohexenyl, octahydronaphthalenyl, and norbornylenyl.

The term "cycloalkyl," as used herein, refers to a saturated monocyclic, bicyclic, or tricyclic hydrocarbon ring system having three to twelve carbon atoms. Representative cycloalkyl groups include, but are not limited to, cyclopropyl, cyclopentyl, bicyclo[3.1.1]heptyl, and adamantyl.

The term "halo" or "halogen," as used herein, refers to F, Cl, Br, or I.

The term "haloalkoxy," as used herein, refers to an alkoxy group substituted with one, two, three, or four halogen atoms.

The term "haloalkyl," as used herein, refers to an alkyl group substituted with one, two, three, or four halogen atoms.

The term "heterocycle," as used herein, represents a monocyclic, bicyclic, or tricyclic ring system wherein one or more rings is a four-, five-, six-, or seven-membered ring containing one, two, or three heteroatoms independently selected from the group consisting of nitrogen, oxygen, and sulfur. Monocyclic ring systems are exemplified by any 3- or 4-membered ring containing a heteroatom independently selected from the group consisting of oxygen, nitrogen and sulfur; or a 5-, 6- or 7-membered ring containing one, two or three heteroatoms wherein the heteroatoms are independently selected from the group consisting of nitrogen, oxygen and sulfur. The 3- and 4-membered rings have no double bonds, the 5-membered ring has from 0–2 double bonds and the 6- and 7-membered rings have from 0–3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, and trithiane. Bicyclic ring systems are exemplified by any of the above monocyclic ring systems fused to an aryl group as defined herein, a cycloalkyl group as defined herein, a cycloalkenyl group, as defined herein, or another monocyclic heterocycle ring system. Representative examples of bicyclic ring systems include, but are not limited to, benzimidazole, benzothiazole, benzothiophene, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, and thiopyranopyridine. Tricyclic rings systems are exemplified by any of the above bicyclic ring systems fused to an aryl group as defined herein, a cycloalkyl group as defined herein, a cycloalkenyl group as defined herein, or another monocyclic heterocycle ring system. Representative examples of tricyclic ring systems include, but are not limited to, acridine, carbazole, carboline, dibenzofuran, dibenzothiophene, naphthofuran, naphthothiophene, oxanthrene, phenazine, phenoxathiin, phenoxazine, phenothiazine, thianthrene, thioxanthene, and xanthene. Heterocycle groups can be attached to the parent molecular moiety through a carbon atom or a nitrogen atom in the ring.

The heterocycle groups of the present invention can be optionally substituted with one, two, three, four, or five substituents independently selected from the group consisting of alkoxy, alkoxyalkyl, alkoxycarbonylalkyl, alkylcarbonyloxy, alkyl, amino, aminoalkyl, cyano, halo, haloalkoxy, haloalkyl, hydroxy, hydroxyalkyl, nitro, and oxo.

The term "hydroxy," as used herein, refers to —OH.

The term "hydroxyalkyl," as used herein, refers to a hydroxy group attached to the parent molecular moiety through an alkyl group.

The term "nitro," as used herein, refers to —NO$_2$.

The term "oxo," as used herein, refers to =O.

The compounds of the present invention can exist as therapeutically acceptable salts. The term "therapeutically acceptable salt," as used herein, refers to salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate, lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to parent compounds of formula (I) for example, by hydrolysis in blood.

Because carbon-carbon double bonds exist in the present compounds, the invention contemplates various geometric isomers and mixtures thereof resulting from the arrangement of substituents around these carbon-carbon double bonds. It should be understood that the invention encompasses both isomeric forms, or mixtures thereof, which possess the ability to inhibit protein kinases. These substituents are designated as being in the E or Z configuration wherein the term "E" represents higher order substituents on opposite sides of the carbon-carbon double bond, and the term "Z" represents higher order substituents on the same side of the carbon-carbon double bond.

In accordance with methods of treatment and pharmaceutical compositions of the invention, the compounds can be administered alone or in combination with other agents. When using the compounds, the specific therapeutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used. The compounds can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrasternal injection.

Parenterally administered aqueous or oleaginous suspensions of the compounds can be formulated with dispersing, wetting, or suspending agents. The injectable preparation can also be an injectable solution or suspension in a diluent or solvent. Among the acceptable diluents or solvents employed are water, saline, Ringer's solution, buffers, monoglycerides, diglycerides, fatty acids such as oleic acid, and fixed oils such as monoglycerides or diglycerides.

The inhibitory effect of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches can also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents, and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes therefore.

Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds with a suitable non-irritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of this invention.

The total daily dose of the compounds administered to a host in single or divided doses can be in amounts from about 0.1 to about 200 mg/kg body weight or preferably from about 0.25 to about 100 mg/kg body weight. Single dose compositions can contain these amounts or submultiples thereof to make up the daily dose.

Preferred compounds of the present invention include, but are not limited to, compounds of formula (I) wherein X is —$CR^x$—; Y is —$CR^y$—; Z is —$CR^z$—; one of $R^x$, $R^y$, $R^z$, and $R^1$ is aryl and the others are hydrogen; and $R^2$ is heterocycle, wherein the heterocycle is other than imidazolyl.

Determination of Biological Activity

The Chk1 enzymatic assay was carried out using recombinant Chk1 kinase domain protein covering amino acids from residue 1 to 289 and a polyhistidine tag at the C-terminal end. Human cdc25c residues 204–225 were used as peptide substrate. The reaction mixture contained 25 mM of HEPES at pH 7.4, 10 mM $MgCl_2$, 0.08 mM Triton X-100, 0.5 mM DTT, 5 µM ATP, 4 nM 33P ATP, 5 µM cdc25c peptide substrate, and 6.3 nM of the recombinant Chk1 protein. Compound vehicle DMSO was maintained at 2% in the final reaction. After 30 minutes at room temperature, the reaction was stopped by addition of equal volume of 4M NaCl and 0.1M EDTA, pH 8. A 40 µL aliquot of the reaction was added to a well in a FlashPlate (NEN Life Science Products, Boston, Mass.) containing 160 µL of phosphate-buffered saline (PBS) without calcium chloride and magnesium chloride and incubated at room temperature for 10 minutes. The plate was then washed 3 times in PBS with 0.05% of Tween-20 and counted in a Packard TopCount counter (Packard BioScience Company, Meriden, Conn.).

Compounds of the present invention inhibited Chk1 at $IC_{50}$ values between about 1 nm and about 10 µM. Preferred compounds inhibited Chk1 at $IC_{50}$ values between about 1 nm and about 1 µM. Thus, the compounds of the invention are useful in treating disorders which are caused or exacerbated by increased protein kinase levels.

Synthetic Methods

Abbreviations which have been used in the descriptions of the scheme and the examples that follow are: $PPh_3$ for triphenylphosphine; dba for dibenzylideneacetone; DME for 1,2-dimethoxyethane; and DMSO for dimethylsulfoxide.

The compounds and processes of the present invention will be better understood in connection with the following synthetic scheme which illustrates the method by which the compounds of the invention may be prepared. Starting materials can be obtained from commercial sources or prepared by well-established literature methods known to those of ordinary skill in the art. The groups X, Y, Z, $R^1$, and $R^2$ are as defined above unless otherwise noted below.

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

Scheme 1

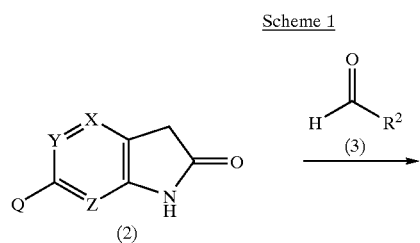

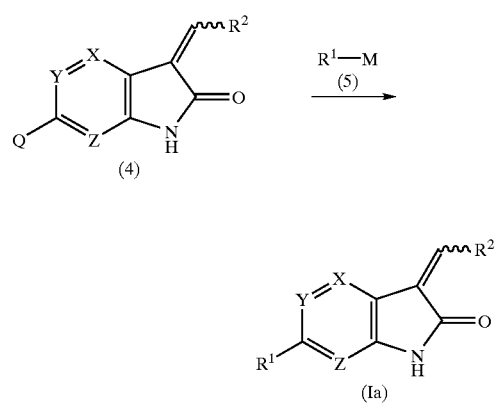

As shown in Scheme 1, compounds of formula (2) (Q is Br or I; X, Y, and Z are —CH— or —N—, provided that at least one of Y and Z is —CH—) can be converted to compounds of formula (4) by treatment with compounds of formula (3) ($R^2$ is as previously defined) in the presence of base. Representative bases include piperidine, dimethylaminopyridine, and pyridine. Examples of solvents used in these reactions include methanol, ethanol, and isopropanol. The reaction is typically conducted at about 25° C. to about 70° C. for about 1 to about 6 hours.

Compounds of formula (4) can be converted to compounds of formula (I) by treatment with compounds of formula (5) (M is $B(OR^3)_2$, wherein $R^3$ is hydrogen or alkyl; or, alternatively, M can be another metal such a trialkylstannane; and $R^1$ is aryl or heterocycle) in the presence of a catalyst and optionally in the presence of a base. Examples of catalysts include $Pd(PPh_3)_4$, $Pd_2(dba)_3$ and triphenylarsine, $Pd_2(dba)_3$ and triphenylphosphine, and $PdCl_2(PPh_3)_2$. Bases used in these reactions include CsF, $Na_2CO_3$, $Cs_2CO_3$, and $K_2CO_3$.

Representative solvents include dioxane, toluene, DME, methanol, and mixtures thereof. The reaction is typically conducted at about 25° C. to about 100° C. for about 6 to about 24 hours.

Scheme 2

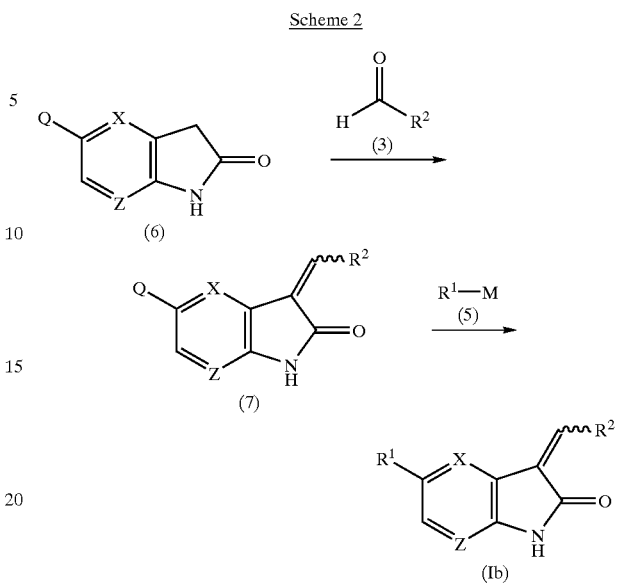

The synthesis of compounds of formula (Ib) is shown in Scheme 2. Compounds of formula (6) (wherein Q is Br or I; and X and Z are selected from the group consisting of —CH— and —N— can be converted to compounds of formula (7) by treatment with compounds of formula (3) under the conditions described in Scheme 1. Compounds of formula (7) can be converted to compounds of formula (Ib) following the procedures described in Scheme 1.

Scheme 3

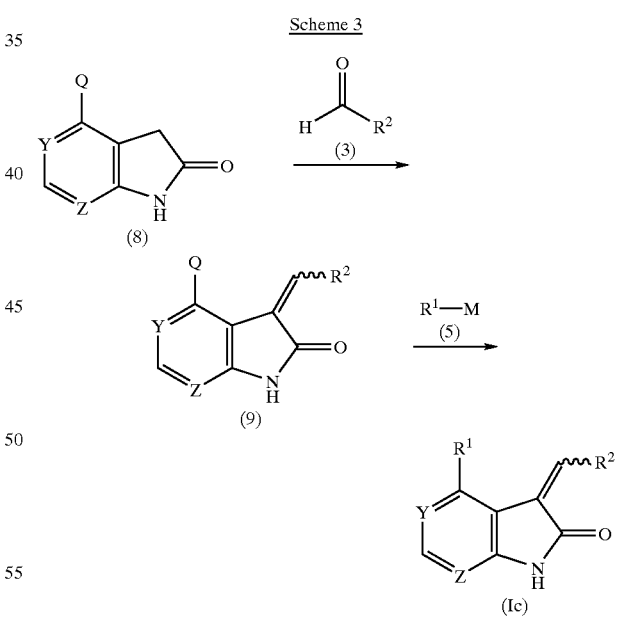

The synthesis of compounds of formula (Ic) is shown in Scheme 3. Compounds of formula (8) (wherein Q is Br or I; and Y and Z are selected from the group consisting of —CH— and —N—, provided that at least one of Y and Z is —CH—, can be converted to compounds of formula (9) by treatment with compounds of formula (3) under the conditions described in Scheme 1. Compounds of formula (9) can be converted to compounds of formula (Ic) following the procedures described in Scheme 1.

Scheme 4

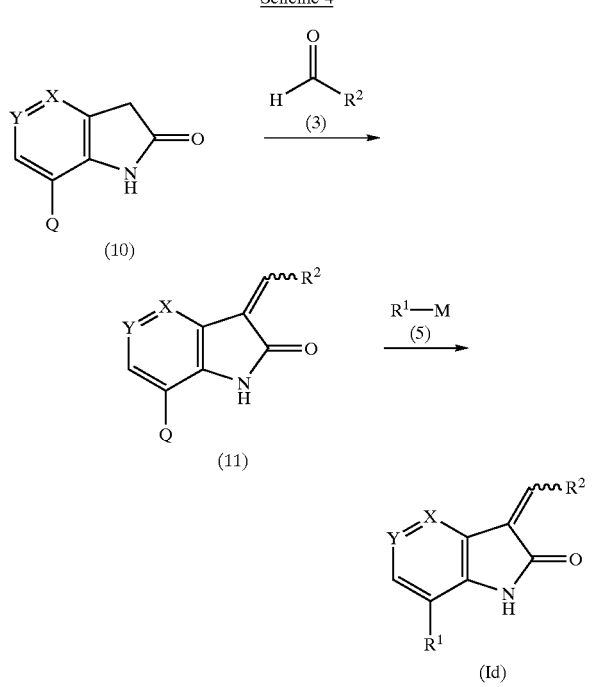

The synthesis of compounds of formula (Id) is shown in Scheme 4. Compounds of formula (10) (wherein Q is Br or I; and X and Y are selected from the group consisting of —CH— and —N— can be converted to compounds of formula (11) by treatment with compounds of formula (3) under the conditions described in Scheme 1. Compounds of formula (11) can be converted to compounds of formula (Id) following the procedures described in Scheme 1.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/ChemSketch version 5.0 (developed by Advanced Chemistry Development, Inc., Toronto, ON, Canada) or were given names which appeared to be consistent with ACD nomenclature.

EXAMPLE 1

(3Z)-6-(4-hydroxy-2-methylphenyl)-3-(1H-pyrrol-2-ylmethylene)-1,3-dihydro-2H-indol-2-one

EXAMPLE 1A (3Z)-6-bromo-3-(1H-pyrrol-2-ylmethylene)-1,3-dihydro-2H-indol-2-one A solution of 6-bromo-1,3-dihydro-2H-indol-2-one (100 mg, 0.47 mmol), 1H-pyrrole-2-carbaldehyde (49.2 mg, 0.52 mmol), and piperidine (0.02 mL, 0.2 mmol) in methanol (3 mL) was stirred at 65° C. for 2 hours, cooled to room temperature, and filtered. The filter cake was washed with hexanes to provide the desired product (65 mg, 48%). MS (DCI/NH$_3$) m/z 290 (M+H)$^+$.

EXAMPLE 1B (3Z)-6-(4-hydroxy-2-methylphenyl)-3-(1H-pyrrol-2-ylmethylene)-1,3-dihydro-2H-indol-2-one A solution of Example 1A (50 mg, 0.17 mmol), 4-{[tert-butyl(dimethyl)silyl]oxy}-2-methylphenylboronic acid (prepared according to the procedure described in WO 01/02369, 55 mg, 0.21 mmol), Pd$_2$(dba)$_3$ (16 mg, 0.017 mmol), and triphenylarsine (31 mg, 0.10 mmol) in 2N Na$_2$CO$_3$ (2 mL) and dioxane (2 mL) was stirred at 80° C. for 18 hours, cooled to room temperature, concentrated, and extracted with ethyl acetate. The combined extracts were washed with brine, dried (MgSO$_4$), filtered, and concentrated. The concentrate was purified by flash column chromatography on silica gel with 70:30 hexanes/ethyl acetate to provide the desired product (6 mg, 8%). MS (DCI/NH$_3$) m/z 317 (M+H)$^+$; $^1$H NMR (500 MHz, DMSO-d$_6$) δ13.32 (s, 1H), 10.85 (s, 1H), 9.33 (s, 1H), 7.73 (s, 1H), 7.63 (d, 1H, J=8.1 Hz), 7.35 (m, 1H), 7.02 (d, 1H, J=8.1 Hz), 6.90 (dd, 1H, J=7.8, 1.5 Hz), 6.83 (m, 1H),6.75 (d, 1H, J=1.5 Hz), 6.68 (d, 1H, J=2.5 Hz), 6.65 (dd, 1H, J=8.1, 2.5 Hz), 6.35 (m, 1H), 3.30 (s, 3H).

EXAMPLE 2

(3Z)-6-(4-hydroxy-3-methoxyphenyl)-3-(pyridin-2-ylmethylene)-1,3-dihydro-2H-indol-2-one

EXAMPLE 2A (3Z)-6-bromo-3-(pyridin-2-ylmethylene)-1,3-dihydro-2H-indol-2-one The desired product was prepared by substituting pyridine-2-carbaldehyde for 1H-pyrrole-2-carbaldehyde in Example 1A (88 mg, 62%). MS (DCI/NH$_3$) m/z 301.1 (M+H)$^+$.

EXAMPLE 2B (3Z)-6-(4-hydroxy-3-methoxyphenyl)-3-(pyridin-2-ylmethylene)-1,3-dihydro-2H-indol-2-one A solution of Example 2A (80 mg, 0.26 mmol), 2-methoxy-4-(4,4,5,5-tetramethyl-1,3,2-dioxaborolan-2-yl)phenol (78 mg, 0.31 mmol), Pd(PPh$_3$)$_4$ (30 mg, 0.026 mmol), and CsF (43 mg, 0.29 mmol) in DME/methanol (2:1) was stirred at 80° C. for 18 hours, cooled to room temperature, concentrated, and extracted with ethyl acetate. The combined extracts were washed with brine, dried (MgSO$_4$), filtered, and concentrated. The concentrate was purified by HPLC (Zorbax C-18 column) with 10–100% acetonitrile/water to provide the desired product (17 mg, 18%). MS (DCI/NH$_3$) m/z 345.1 (M+H)$^+$; $^1$H NMR (300 MHz, CD$_3$OD) δ8.92 (d, 1H, J=5.5 Hz), 8.82 (d, 1H, J=7.8 Hz), 8.25 (s, 1H), 7.89 (m, 1H), 7.71 (s, 1H), 7.62 (m, 1H), 7.41 (m, 1H), 7.24 (d, 1H, J=1.7 Hz), 7.14 (dd, 1H, J=8.1, 2.0 Hz), 7.08 (dd, 1H, J=5.8, 2.1 Hz), 6.99 (d, 1H, J=8.1 Hz), 3.98 (s, 3H); Anal. Calcd. for C$_{21}$H$_{16}$N$_2$O$_3$.1.5CF$_3$CO$_2$H: C, 73.24; H, 4.68; N, 8.13. Found: C, 56.40; H, 3.57; N, 5.005.

EXAMPLE 3

(3Z)-5-(4-hydroxy-3-methoxyphenyl)-3-(1H-pyrrol-2-ylmethylene)-1,3-dihydro-2H-indol-2-one

EXAMPLE 3A (3Z)-5-bromo-3-(1H-pyrrol-2-ylmethylene)-1,3-dihydro-2H-indol-2-one The desired product was prepared by substituting 5-bromo-1,3-dihydro-2H-indol-2-one for 6-bromo-1,3-dihydro-2H-indol-2-one in Example 1A.

EXAMPLE 3B (3Z)-5-(4-hydroxy-3-methoxyphenyl)-3-(1H-pyrrol-2-ylmethylene)-1,3-dihydro-2H-indol-2-one The desired product was prepared by substituting Example 3A for Example 2A in Example 2B (8 mg, 13%). HRMS (DCI/NH$_3$) m/z 333.1 (M+H)$^+$; $^1$H NMR (500 MHz, CD$_3$OD): δ7.75 (d, 1H, J=1.5 Hz), 7.69 (s, 1H), 7.35 (dd, 1H, J=8.1 Hz, 1.5 Hz), 7.21 (m, 1H), 7.17 (d, 1H, J=2.2 Hz), 7.07 (dd, 1H, J=8.1 Hz, 2.2 Hz), 6.94 (d, 1H, J=8.1 Hz), 6.85 (d, 1H, J=8.2 Hz), 6.82 (m, 1H), 6.35 (m, 1H) 3.94 (s, 3H).

EXAMPLE 4

(3Z)-3-[(3,5-dimethyl-1H-pyrrol-2-yl)methylene]-6-(4-hydroxy-3-methoxyphenyl)-1,3-dihydro-2H-indol-2-one

EXAMPLE 4A (3Z)-6-bromo-3-[(3,5-dimethyl-1H-pyrrol-2-yl)methylene]-1,3-dihydro-2H-indol-2-one The desired product was prepared by substituting 3,5-dimethyl-1H-pyrrole-2-carbaldehyde for 1H-pyrrole-2-carbaldehyde in Example 1A.

EXAMPLE 4B (3Z)-3-[(3,5-dimethyl-1H-pyrrol-2-yl)methylene]-6-(4-hydroxy-3-methoxyphenyl)-1,3-dihydro-2H-indol-2-one The desired product was prepared by substituting Example 4A for Example 2A in Example 2B (15 mg, 13%). HRMS (DCI/NH$_3$) m/z 361.1 (M+H)$^+$; $^1$H NMR (500 MHz, DMSO-d$_6$) δ13.31 (s, 1H), 10.78 (s, 1H), 9.04 (s, 1H), 7.72 (d, 1H, J=8.1 Hz), 7.55 (s, 1H), 7.23 (dd, 1H, J=7.8 Hz, 1.6 Hz), 7.15 (d, 1H, J=2.2 Hz), 7.06 (d, 1H, J=2.2 Hz), 7.05 (dd, 1H, J=8.4 Hz, 2.2 Hz), 6.85 (d, 1H, J=8.1 Hz), 6.01 (m, 1H), 3.86 (s, 3H), 2.33 (s, 3H), 2.31 (s, 3H); Anal. Calcd. for C$_{22}$H$_{20}$N$_2$O$_3$.0.2 CF$_3$CO$_2$H.0.1H$_2$O: C, 73.32; H, 5.59; N, 7.77; Found: C, 69.87; H, 5.27; N, 7.14.

EXAMPLE 5

(3Z)-6-(4-hydroxy-3-methoxyphenyl)-3-(1H-pyrrol-2-ylmethylene)-1,3-dihydro-2H-indol-2-one The desired product was prepared by substituting Example 1A for Example 2A in Example 2B (8 mg, 9%). HRMS (DCI/NH$_3$) m/z 333 (M+H)$^+$; $^1$H NMR (500 MHz, CDCl$_3$) δ13.23 (s, 1H), 7.65 (s, 1H), 5.63 (s, 1H), 7.51 (d, 1H, J=8.1 Hz), 7.44 (s, 1H), 7.24 (d, 1H, J=1.5 Hz), 7.19 (m, 1H), 7.11 (dd, 1H, J=8.1 Hz, 1.8 Hz), 7.08 (d, 1H, J=1.8 Hz), 7.07 (dd, 1H, J=7.5 Hz, 1.8 Hz), 6.99 (d, 1H, J=8.1 Hz), 6.79 (m, 1H), 6.40 (m, 1H), 3.97 (s, 3H).

EXAMPLE 6

(3Z)-6-(4-hydroxy-3-methoxyphenyl)-3-[(7-methyl-1H-indol-3-yl)methylene]-1,3-dihydro-2H-indol-2-one

EXAMPLE 6A (3Z)-6-bromo-3-[(7-methyl-1H-indol-3-yl)methylene]-1,3-dihydro-2H-indol-2-one The desired product was prepared by substituting 7-methyl-1H-indole-3-carbaldehyde for 1H-pyrrole-2-carbaldehyde in Example 1A.

EXAMPLE 6B (3Z)-6-(4-hydroxy-3-methoxyphenyl)-3-[(7-methyl-1H-indol-3-yl)methylene]-1,3-dihydro-2H-indol-2-one The desired product was prepared by substituting Example 6A for Example 2A in Example 2B (27 mg, 16%). HRMS (DCI/NH$_3$) m/z 397.1 (M+H)$^+$; $^1$H NMR (400 MHz, DMSO-d$_6$) δ11.97 (s, 1H), 10.50 (s, 1H), 9.43 (d, 1H, J=3.1 Hz), 9.07 (s, 1H), 8.11 (s, 1H), 8.00 (d, 1H, J=7.6 Hz), 7.89 (d, 1H, J=8.0 Hz), 7.25 (dd, 1H, J=8 Hz, 1.5 Hz), 7.18 (d, 1H, J=2.1 Hz), 7.13 (d, 1H, J=8 Hz), 7.07 (dd, 1H, J=8.3 Hz, 2.1 Hz), 7.04 (d, 1H, J=1.2 Hz), 6.86 (d, 1H, J=8.2 Hz), 3.87 (s, 3H), 2.53 (s, 3H); Anal. Calcd. for C$_{25}$H$_{20}$N$_2$O$_3$.0.25CF$_3$CO$_2$H: C, 75.74; H, 5.08; N, 7.0; Found: C, 72.31; H, 4.63; N, 6.85.

EXAMPLE 7

(3Z)-6-(4-hydroxy-3-methoxyphenyl)-3-(1H-indol-3-ylmethylene)-1,3-dihydro-2H-indol-2-one

EXAMPLE 7A (3Z)-6-bromo-3-(1H-indol-3-ylmethylene)-1,3-dihydro-2H-indol-2-one The desired product was prepared by substituting 1H-indole-3-carbaldehyde for 1H-pyrrole-2-carbaldehyde in Example 1A.

EXAMPLE 7B (3Z)-6-(4-hydroxy-3-methoxyphenyl)-3-(1H-indol-3-ylmethylene)-1,3-dihydro-2H-indol-2-one The desired product was prepared by substituting Example 7A for Example 2A in Example 2B (9 mg, 7%). HRMS (DCI/NH$_3$) m/z 383.1 (M+H)$^+$; $^1$H NMR (400 MHz, DMSO-d$_6$) δ12.01 (s, 1H), 10.48 (s, 1H), 9.14 (s, 1H), 8.24 (d, 1H, J=3.1 Hz), 7.86 (s, 1H), 7.77 (d, 1H, J=8 Hz), 7.68 (d, 1H, J=6.6 Hz), 7.55 (dd, 1H, J=8 Hz, 0.9 Hz), 7.26 (dd, 1H, J=7.9 Hz, 0.9 Hz), 7.21 (m, 1H), 7.18 (d, 1H, J=2.1 Hz), 7.08 (dd, 1H, J=8.9 Hz, 1.6 Hz), 7.07 (d, 1H, J=2.2 Hz), 6.86 (d, 1H, J=8.3 Hz), 3.87 (s, 3H); Anal. Calcd. for C$_{24}$H$_{18}$N$_2$O$_3$.0.35CF$_3$CO$_2$H.0.05H$_2$O: C, 75.38; H, 4.74; N, 7.33; Found: C, 70.58; H, 4.22; N, 6.12.

EXAMPLE 8

(3Z)-6-(4-hydroxy-3-methoxyphenyl)-3-(1H-pyrrolo[2,3-b]pyridin-3-ylmethylene)-1,3-dihydro-2H-indol-2-one

EXAMPLE 8A (3Z)-6-bromo-3-(1H-pyrrolo[2,3-b]pyridin-3-ylmethylene)-1,3-dihydro-2H-indol-2-one The desired product was prepared by substituting 1H-pyrrolo[2,3-b]pyridine-3-carbaldehyde for 1H-pyrrole-2-carbaldehyde in Example 1A.

EXAMPLE 8B (3Z)-6-(4-hydroxy-3-methoxyphenyl)-3-(1H-pyrrolo[2,3-b]pyridin-3-ylmethylene)-1,3-dihydro-2H-indol-2-one The desired product was prepared by substituting Example 8A for Example 2A in Example 2B (2 mg, 2%).

HRMS (ESI) m/z 382.1 (M−H)⁻; ¹H NMR (500 MHz, DMSO-d₆) δ12.47 (s, 1H), 10.57 (s, 1H), 9.50 (d, 1H, J=2.8 Hz), 8.63 (dd, 1H, J=7.8 Hz, 1.3 Hz), 8.36 (dd, 1H, J=4.7 Hz, 1.3 Hz), 8.13 (s, 1H), 7.90 (d, 1H, J=8.1 Hz), 7.30 (m, 1H), 7.27 (dd, 1H, J=7.8 Hz, 1.5 Hz), 7.19 (d, 1H, J=1.9 Hz), 7.10 (dd, 1H, J=7.2 Hz, 2.2 Hz), 7.07 (d, 1H, J=2.2 Hz), 7.05 (d, 1H, J=1.6 Hz), 6.86 (d, 1H, J=8.1 Hz), 6.80 (d, 1H, J=8.1 Hz), 3.87 (s, 3H).

EXAMPLE 9 methyl 3-(5-{(Z)-[6-(4-hydroxy-3-methoxyphenyl)-2-oxo-1,2-dihydro-3H-indol-3-ylidene]methyl}-2,4-dimethyl-1H-pyrrol-3-yl)propanoate

EXAMPLE 9A methyl 3-(5-formyl-2,4-dimethyl-1H-pyrrol-3-yl)propanoate

The desired product was prepared according to the procedure described in *J. Heterocyclic Chem.*, 20 1983, 1383.

EXAMPLE 9B methyl 3-{5-[(Z)-(6-bromo-2-oxo-1,2-dihydro-3H-indol-3-ylidene)methyl]-2,4-dimethyl-1H-pyrrol-3-yl}propanoate The desired product was prepared by substituting Example 9A for 1H-pyrrole-2-carbaldehyde in Example 1A.

EXAMPLE 9C methyl 3-(5-{(Z)-[6-(4-hydroxy-3-methoxyphenyl)-2-oxo-1,2-dihydro-3H-indol-3-ylidene]methyl}-2,4-dimethyl-1H-pyrrol-3-yl)propanoate The desired product was prepared by substituting Example 9B for Example 2A in Example 2B (9 mg, 5%). HRMS (ESI) m/z 447.0 (M+H)⁺; ¹H NMR (500 MHz, DMSO-d₆) δ13.35 (s, 1H), 10.75 (s, 1H), 9.04 (s, 1H), 7.73 (d, 1H, J=7.8 Hz), 7.54 (s, 1H), 7.22 (dd, 1H, J=8.1 Hz, 1.6 Hz), 7.14 (d, 1H, J=1.8 Hz), 7.05–7.03 (m, 2H), 6.85 (d, 1H, J=8.1 Hz), 3.85 (s, 3H), 3.59 (s, 3H), 2.68 (t, 2H), 2.46 (t, 2H), 2.29 (s, 3H), 2.26 (s, 3H).

EXAMPLE 10

(3Z)-6-(4-hydroxy-3-methoxyphenyl)-3-[(3-isopropyl-5-methyl-1H-pyrrol-2-yl)methylene]-1,3-dihydro-2H-indol-2-one

EXAMPLE 10A (3Z)-6-bromo-3-[(3-isopropyl-5-methyl-1H-pyrrol-2-yl)methylene]-1,3-dihydro-2H-indol-2-one The desired product was prepared by substituting 3-isopropyl-5-methyl-1H-pyrrole-2-carbaldehyde for 1H-pyrrole-2-carbaldehyde in Example 1A.

EXAMPLE 10B (3Z)-6-(4-hydroxy-3-methoxyphenyl)-3-[(3-isopropyl-5-methyl-1H-pyrrol-2-yl)methylene]-1,3-dihydro-2H-indol-2-one The desired product was prepared by substituting Example 10A for Example 2A in Example 2B (50 mg, 44%). HRMS (DCI/NH₃) m/z 389.2 (M+H)⁺; ¹H NMR (500 MHz, DMSO-d₆) δ13.37 (s, 1H), 10.78 (s, 1H), 9.04 (s, 1H), 7.74 (d, 1H, J=8.2 Hz), 7.58 (s, 1H), 7.22 (dd, 1H, J=8.1 Hz, 1.5 Hz), 7.15 (d, 1H, J=2.2 Hz), 7.05 (d, 1H, J=1.2 Hz), 7.04 (dd, 1H, J=7.1 Hz, 2.2 Hz), 6.85 (d, 1H, J=8.1 Hz), 6.09 (d, 1H, J=2.5 Hz), 3.86 (s, 3H), 3.35 (m, 1H), 2.34 (s, 3H), 1.23 (s, 3H), 1.21 (s, 3H); Anal. Calcd. for C₂₄H₂₄N₂O₃.0.4 H₂O: C, 74.21; H, 6.23; N, 7.21. Found: C, 72.58; H, 6.01; N, 6.87.

EXAMPLE 12

(3Z)-3-{[4-(2-hydroxyethyl)-3,5-dimethyl-1H-pyrrol-2-yl]methylene}-6-(4-hydroxy-3-methoxyphenyl)-1,3-dihydro-2H-indol-2-one

EXAMPLE 12A (3Z)-6-bromo-3-{[4-(2-hydroxyethyl)-3,5-dimethyl-1H-pyrrol-2-yl]methylene}-1,3-dihydro-2H-indol-2-one The desired product was prepared by substituting 4-(2-hydroxyethyl)-3,5-dimethyl-1H-pyrrole-2-carbaldehyde for 1H-pyrrole-2-carbaldehyde in Example 1A.

EXAMPLE 12B (3Z)-3-{[4-(2-hydroxyethyl)-3,5-dimethyl-1H-pyrrol-2-yl]methylene}-6-(4-hydroxy-3-methoxyphenyl)-1,3-dihydro-2H-indol-2-one The desired product was prepared by substituting Example 12A for Example 2A in Example 2B (23 mg, 15%). HRMS (DCI/NH₃) m/z 405.1 (M+H)⁺; ¹H NMR (500 MHz, DMSO-d₆) δ13.36 (s, 1H), 10.73 (s, 1H), 9.03 (s, 1H), 7.72 (d, 1H, J=8.1 Hz), 7.54 (s, 1H), 7.22 (dd, 1H, J=7.8 Hz, 1.6 Hz), 7.15 (d, 1H, J=1.9 Hz), 7.05 (d, 1H, J=1.0 Hz), 7.04 (dd, 1H, J=6.9 Hz, 1.9 Hz), 6.85 (d, 1H, J=8.2 Hz), 3.86 (s, 3H), 3.43 (t, 2H), 2.56 (t, 2H), 2.30 (s, 3H), 2.26 (s, 3H); Anal. Calcd. for C₂₄H₂₄N₂O₄.0.15 CF₃CO₂H.0.05 H₂O: C, 71.27; H, 5.98; N, 6.93 Found: C, 68.97; H, 5.62; N, 6.68.

EXAMPLE 13

(3Z)-3-({4-[(dimethylamino)methyl]-3-isopropyl-5-methyl-1H-pyrrol-2-yl}methylene)-6-(4-hydroxy-3-methoxyphenyl)-1,3-dihydro-2H-indol-2-one

EXAMPLE 13A (3Z)-6-bromo-3-({4-[(dimethylamino)methyl]-3-isopropyl-5-methyl-1H-pyrrol-2-yl}methylene)-1,3-dihydro-2H-indol-2-one The desired product was prepared by substituting 4-[(dimethylamino)methyl]-3-isopropyl-5-methyl-1H-pyrrole-2-carbaldehyde for 1H-pyrrole-2-carbaldehyde in Example 1A.

EXAMPLE 13B (3Z)-3-({4-[(dimethylamino)methyl]-3-isopropyl-5-methyl-1H-pyrrol-2-yl}methylene)-6-(4-hydroxy-3-methoxyphenyl)-1,3-dihydro-2H-indol-2-one The desired product was prepared by substituting Example 13A for Example 2A in Example 2B (8 mg, 7%).

HRMS (ESI) m/z 444.2 (M−H)⁻; ¹H NMR (500 MHz, DMSO) δ13.84 (s, 1H), 10.97 (s, 1H), 9.11 (br s, 1H), 9.00 (br s, 1H), 7.66 (s, 1H), 7.26 (dd, 1H, J=7.8 Hz, 1.6 Hz), 7.15 (d, 1H, J=2.2 Hz), 7.08 (d, 1H, J=1.5 Hz), 7.05 (dd, 1H, J=8.1 Hz, 2.2 Hz), 6.86 (d, 1H, J=8.4 Hz), 4.21 (s, 1H), 4.20 (s, 1H), 3.86 (s, 3H), 3.26 (m, 1H), 2.79 (s, 3H), 2.78 (s, 3H), 2.41 (s, 3H), 1.42 (s, 3H), 1.41 (s, 3H); Anal. Calcd. for $C_{27}H_{31}N_3O_3 \cdot 2CF_3CO_2H$: C, 72.78; H, 7.01; N, 9.43. Found: C, 55.17; H, 4.62; N, 6.08.

EXAMPLE 14

(3Z)-6-(4-hydroxy-2-methoxyphenyl)-3-(1H-pyrrol-2-ylmethylene)-1,3-dihydro-2H-indol-2-one The desired product was prepared by substituting Example 1A and 4-hydroxy-2-methoxyphenylboronic acid for Example 2A and 2-methoxy-4-(4,4,5,5-tetramethyl-1,3,2-dioxaborolan-2-yl)phenol, respectively, in Example 2B (7 mg, 14%). HRMS (DCI/NH₃) m/z 333.1 (M+H)⁺; ¹H NMR (400 MHz, DMSO-d₆) δ13.32 (s, 1H), 10.82 (s, 1H), 9.54 (s, 1H), 7.69 (s, 1H), 7.59 (d, 1H, J=7.7 Hz), 7.34 (m, 1H), 7.10 (d, 1H, J=8.0 Hz), 7.04 (dd, 1H, J=8.0 Hz, 1.5 Hz), 6.96 (d, 1H, J=1.6 Hz), 6.82 (m, 1H), 6.51 (d, 1H, J=2.1 Hz), 6.44 (dd, 1H, J=8.3 Hz, 2.1 Hz), 6.35 (m, 1H), 3.72 (s, 1H).

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

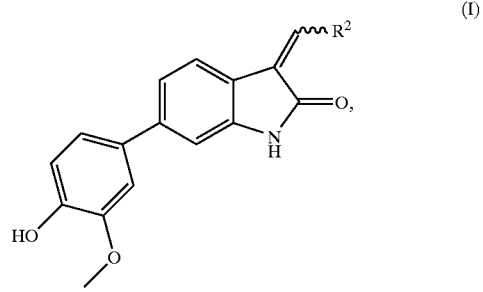

or a therapeutically acceptable salt thereof, wherein
R¹ is selected from unsubstituted and substituted pyrollopyridinyl, unsubstituted and substituted indolyl, unsubstituted and substituted pyridinyl and unsubstituted pyrrolyl.

2. The compound of claim 1 wherein the heterocycle is selected from the group consisting of unsubstituted and substituted pyrrolopyridinyl, and unsubstituted pyrrolyl.

3. The compound of claim 1 which is
(3Z)-6-(4-hydroxy-3-methoxyphenyl)-3-(1H-pyrrolo[2,3-b]pyridin-3-ylmethylene)-1,3-dihydro-2H-indol-2-one.

4. The compound of claim 1 wherein the heterocycle is selected from the group consisting of unsubstituted and substituted indolyl and unsubstituted and substituted pyridinyl.

5. The compound of claim 4 selected from the group consisting of
(3E)-6-(4-hydroxy-3-methoxyphenyl)-3-(pyridin-2-ylmethylene)-1,3-dihydro-2H-indol-2-one;
(3Z)-6-(4-hydroxy-3-methoxyphenyl)-3-[(7-methyl-1H-indol-3-yl)methylene]-1,3-dihydro-2H-indol-2-one; and
(3Z)-6-(4-hydroxy-3-methoxyphenyl)-3-(1H-indol-3-ylmethylene)-1,3-dihydro-2H-indol-2-one.

\* \* \* \* \*

UNITED STATES PATENT AND TRADEMARK OFFICE
CERTIFICATE OF CORRECTION

PATENT NO. : 6,797,825 B2
DATED : September 28, 2004
INVENTOR(S) : Nan-Horng Lin et al.

It is certified that error appears in the above-identified patent and that said Letters Patent is hereby corrected as shown below:

Column 16,
Line 17, replace "R1" with -- R2 --.

Signed and Sealed this

Twenty-first Day of February, 2006

JON W. DUDAS
*Director of the United States Patent and Trademark Office*